United States Patent [19]

Chu et al.

[11] Patent Number: 5,338,758
[45] Date of Patent: Aug. 16, 1994

[54] BICYCLIC DITERPENE PAF ANTAGONIST COMPOUNDS

[75] Inventors: Min Chu, Union; Mahesh Patel, Verona; Ann C. Horan, Summit; Vincent P. Gullo, Liberty Corner, all of N.J.

[73] Assignee: Schering Corporation, Kenilworth, N.J.

[21] Appl. No.: 954,414

[22] Filed: Sep. 30, 1992

Related U.S. Application Data

[63] Continuation-in-part of Ser. No. 863,275, Apr. 3, 1992, abandoned.

[51] Int. Cl.$^5$ .................. C07D 307/77; A61K 31/34
[52] U.S. Cl. ..................................... 514/468; 514/766; 549/457; 549/459; 585/360
[58] Field of Search ................ 549/457, 459; 585/360; 514/468, 766

[56] References Cited

PUBLICATIONS

Karlsson, B., et al. Tetrahedron (1978) vol. 34 pp. 2349–2354.

Chem Abstracts (1992) 116: 57549d–Corresponds to Japanese Kokai JP 03,216,197 (91,216,197).

*Primary Examiner*—Johann Richter
*Assistant Examiner*—John Peabody
*Attorney, Agent, or Firm*—Thomas D. Hoffman

[57] ABSTRACT

Four bicyclic terpenes isolated from a culture broth of Phoma sp SCF0592, ATCC 74077, pharmaceutical compositions containing them and their use as PAF antagonists to treat allergic and inflammatory diseases are disclosed.

2 Claims, No Drawings

BICYCLIC DITERPENE PAF ANTAGONIST COMPOUNDS

CROSS-REFERENCE TO RELATED APPLICATOIN

This application is a continuation-in-part application of commonly-owned U.S. patent application Ser. No. 07/863,275, filed Apr. 3, 1992, now abandoned.

BACKGROUND OF THE INVENTION

This invention relates to novel bicyclic diterpene compounds useful as PAF antagonists, antihistamines and antiinflammatory agents. The compounds are isolated from a PAF antagonist complex which is produced in fermentation under controlled conditions, using a biologically pure culture of the microorganism Phoma sp. SCF0592, ATCC 74077.

B. Karlsson et al. in *Tetrahedron* (1978), 34, 2349 disclose a bicyclic diterpene, verticillol represented by formula A

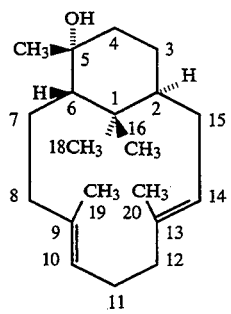

Verticillol is disclosed as a plant natural product, which follows the isoprene rule, isolated from the wood of *Sciadopitys verticilla* Sieb et Zucc (Taxodiaceae). This reference does not disclose any biological activity for verticillol and does not disclose or make obvious the bicyclic diterpene compounds of this invention.

Japanese Kokai J P 03,216,197 (91,216,197), published Sept. 24, 1991, discloses a bicyclic compound, phomactin B, represented by the formula B

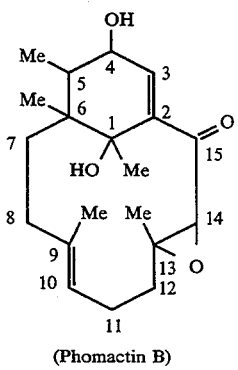

(Phomactin B)

Phomactin B is disclosed as a PAF antagonist which was produced by fermentation of Phoma sp. SANK 11486 (FERM BP-2598).

Neither reference discloses the compounds of this invention.

SUMMARY OF THIS INVENTION

The present invention provides a compound represented by the formulas I to IV

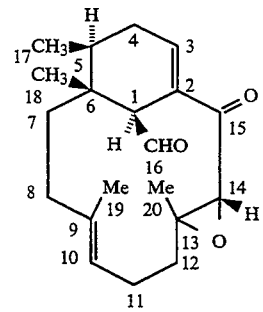

I

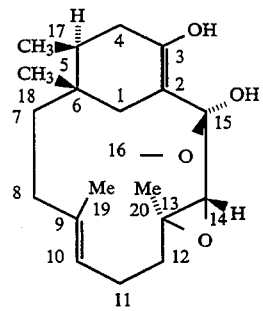

II

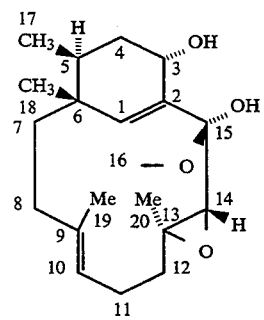

III or

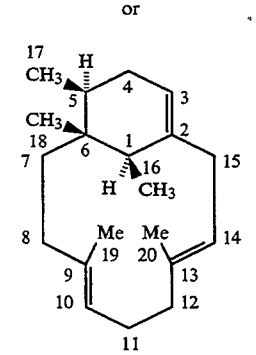

IV in substantially chemically pure form.

The present invention also provides pharmaceutical compositions containing the compounds of Formulas I, II, III or IV as well as methods of treating a disease wherein platelet-activating factor ("PAF") is implicated as a factor or agent by administering a PAF antagonist effective amount of a compound of formulas I, II, III or IV In another aspect of the present invention, there is provided a biologically pure culture of the microorganism Phoma sp. SCF0592, ATCC 74077 as well as mutants and variants thereof which are capable of producing the PAF antagonist active complex in a recoverable quantity upon fermentation, under aerobic conditions in an aqueous medium containing assimilable sources of nitrogen and carbon.

Another aspect of the present invention is directed to the PAF antagonist active complex produced by cultivating a strain of Phoma sp., SCF0592, ATCC 74077 in a pH and temperature controlled medium having assimilable sources of carbon and nitrogen under controlled aerobic conditions until a composition of matter having substantial PAF antagonist activity is produced.

THE MICROORGANISM

The microorganism used for the production of the PAF antagonist active complex and the compounds represented by formulas I–IV is a biologically pure culture of Phoma sp. SCF0592, ATCC 74077.

A viable culture of this microorganism has been deposited on Jun. 26, 1991 in the collection of the American Type Culture Collection (ATCC) in Rockville, Md., where it has been assigned accession number ATCC 74077. Should the deposited culture become lost, destroyed or non-viable during the longer of the thirty (30) year period from the date of the culture was deposited or the five (5) year period after the last request for the deposited culture or the effective life of the patent which issues from this application, the culture will be replaced, upon notice, by applicants or assignee(s) of this application. Subcultures of Phoma, sp. SCF0592, ATCC 74077 are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the US Patent Laws.

The microorganism was isolated from a leaf litter sample of mixed *Quercus* species, i.e., *Q. falcata* var *pagodafolia*, *Q. michauxii* and *Q. nigra*. The sample was collected in a second growth mixed hardwood lot in Baton Rouge, La.

The producing culture of this invention, SCF0592, is a species of the genus Phoma. Phoma is a genus in the order Sphaeropsidales of the class Deuteromycetes.

THE CULTURAL CHARACTERISTICS OF THE PRODUCING CULTURE OF THIS INVENTION, SCF0592.

Agar plugs, 2×2 mm, from 10 to 14 day old malt extract agar slants, incubated at 22° C., were used as the inoculum for morphological and cultural characterisitics of the producing culture of this invention, SCF0592. Morphological characterisitcs of SCF0592 were observed on plates of malt extract agar incubated at 22° C. for 10 to 12 days. Culture characterisitics of SCF0592 were observed on petri dishes containing malt extract, malt yeast, potato dextrose, Czapek's Dox, yeast extract-peptone-dextrose and corn meal agars after 12 days at 22° C. in the dark.

Morphological examination of the producing culture on malt extract agar reveals unilocular pycnidia, superficial or slightly immersed in the agar. The pycnidia occur singly or in clusters, are subglobose, pale becoming medium brown. Mature pycnidia average 100 microns in height and 125 microns in diameter with a single central ostiole. Conidiophores are absent; the conidia are aseptate, hyaline, thin-walled, 1.5–2×2.5–3 microns, ellipsoid and often biguttulate. Multicellular setae, 20×3 μm, may be present near the ostiole.

On malt extract agar, colonies grew to 33 mm in diameter and appeared humped in the center and velutinous. Hyaline aerial mycelia were formed along with blackish brown submerged mycelia. Pycnidia were absent from margins but were numerous and large in other regions of the colony.

On malt yeast agar, colonies grew to 42 mm in diameter, were low spreading and velutinous in older regions. Aerial mycelia were hyaline, lanose and in sectors, with blackish brown submerged mycelia in older regions and sectors. Pycnidia were abundant.

Colonies on potato dextrose agar, reached 44 mm in diameter, were low and spreading. Colony color was medium brown to dark olive on the surface and dark brown, typically zonate, in reverse. Hyaline aerial mycelia were formed as were abundant pycnidia.

On Czapek's Dox agar, colonies grew to 47 mm in diameter, were low and spreading. Colony color was drab olive on the surface and darker with marked zonation in reverse. The aerial mycelia were hyaline with brown submerged mycelia. Pycnidia were absent from the colony margin but numerous in other regions of the colony.

On yeast extract-peptone-dextrose agar, the colonies grew to 37 mm in diameter and were low and reduced, and were wrinkled in texture with no sectoring. The colony color was medium brown in reverse. Hyaline aerial mycelia were formed. Pycnidia were absent.

On corn meal agar, the colonies grew to 29 mm in diameter and appeared velutinous and wrinkled. Zonation was absent but the colonies were heavily felted in sectors. Hyaline aerial mycelia were formed along with dark brown submerged mycelia. Dense stroma of thick-walled, beaded hyphae with immersed pycnidia were formed.

Based on the above-listed characteristics and a comparison with the relevant generic characteristics for Phoma listed in "The Coelomycetes" by B. C. Sutton, CMI 1980 at page 379, we conclude that the producing culture of this invention is a species of the genus Phoma.

FERMENTATION OF THE MICROORGANISM

The PAF active complex of this invention is produced when the producing microorganism, Phoma sp. SCF0592, ATCC 74077 is grown in an aqueous nutrient medium under submerged aerobic conditions at a temperature of about 27° C. to 40° C., preferably at from 27° C. to 35° C., and at a pH of from about 6.5 to 8.0 with agitation until substantial PAF activity is imparted to the medium. Temperature studies indicate that the organism grows rapidly at about 30° C. Therefore, the fermentation is preferably conducted employing a single temperature pattern of about 30° C. for a period of about 24 to about 96 hours preferably about 90 hours in flasks. A larger scale fermentation is generally conducted from about 3 to 7 days, preferably for about 5 days in tank.

The growth of the organism (packed cell volume), pH and dissolved oxygen levels are determined either intermittently or continuously. During the course of the fermentation, production of the PAF-active complex was monitored by the PAF-induced platelet aggregation assay of the whole broth.

As nutrient medium, there is employed any suitable medium containing a source of carbon, for example an assimilable carbohydrate, and a source of nitrogen, for example an assimilable nitrogenous or proteinaceous material and various mineral salts.

The medium employed for the fermentation contained proteose peptone, yeast extract, cerelose and soy grits as the major sources of nitrogen and carbon, respectively. Under these conditions, the microorganism, SCF0592. produced PAF active complex containing at least four biologically active components as determined by monitoring the fermenlation using the PAF-induced platelet aggregation assay.

The foregoing media are exemplary of the nutrients utilized by Phoma sp to produce PAF active complex. However it is obvious to those trained in fermentation science that a wide range of nutrients obtained from a number of suppliers may be substituted for the foregoing, and that generally good growth and production can be obtained, such nutrients being the functional equivalent to those set forth herein.

The fermentation is generally conducted by initially sterilizing the fermentation medium prior to the addition of the inoculum.

During the course of a typical fermentation, the pH decreased from 8 to 4 within 18 hours, accompanied by a similarly rapid drop in the dissolved oxygen concentration. PAF activity was detected at this point and reached a maximum after 120 hours. At this point of maximal PAF activity, the dissolved oxygen concentration was zero and the packed cell volume was its maximum. The fermentation broth was normally harvested at this optimal point.

Prior to sterilization, the pH of the medium is usually adjusted to 7.

The fermentation was initiated by addition of the inoculum to the broth. Generally, inoculum volume is between 3.5 to 7.0% of total broth volume. The inoculum is prepared by addition of a sample of 5% inoculum of the frozen whole broth of the producing culture to an appropriate germination medium. A particularly preferred germination medium in grams/liter comprises proteose peptone #3, 5.0; sodium chloride 5.0; cerelose, 20.0 yeast extract, 3.0; soy grits, 5.0 and sodium potassium phosphate (monobasic) 5.0. The inoculum stage of the fermentation usually requires from 24 to 120 hours with 48-72 hours being preferred and is generally conducted at about 30° C. with agitation (300 rpm). A 7% inoculum of this culture is transferred to the same germination medium and grown as described hereinabove. Inoculum developed in this manner is transferred to the fermentation medium. A particularly preferred fermentation medium comprises 10 g/l of neopeptone ano 40 g/l of cerelose. Agitation (400 rpm), a positive air flow, generally about 4.5 L/min. and a temperature of about 30° C. are employed during the five day fermentation. The pH of the solution is adjusted to 7. An antifoam agent such as SAG (Union Carbide Corp., 50% solution) is added, if necessary, to the fermentors to control foam. A PAF-active complex containing at least 4 components as detected by the PAF-induced platelet aggregation assay is produced.

ISOLATION AND PURIFICATION OF THE PAF ACTIVE COMPLEX AND OF THE COMPOUNDS OF THIS INVENTION

The purification of the bicyclic diterpenes compounds of formulas I to IV was accomplished by ethyl acetate extraction, gel permeation and reverse phase chromatography.

The fermentation broth (20 L) was extracted with ethyl acetate without pH adjustment. The extract was evaporated in vacuo to give 7 grams of a brown syrup. The syrup was dissolved in a minimum amount of dichioromethane-methanol (7:3 v/v) solvent mixture and loaded onto a LH-20 Sephadex column. The column was eluted with the same solvent mixture. The early PAF active fractions which contained mainly the compound of formula I were combined based on TLC analysis. The solvent volume was reduced until precipitation occurred. The pale yellow solid was readily precipitated by the addition of methanol, and then recrystallized with chloroform: methanol (3:7 v/v) to afford pure compound of formula I. The later fractions were obtained as an PAF active complex. Pure compound IV was isolated from this complex by the same precipitation and recrystallization procedures used to obtain compound I. The combined mother liquors from both precipitations were dried, and the residue was further purified by two consecutive CHP-20P gel columns. The first was eluted with 0-100% aqueous MeOH gradient, and the second with 0-80% aqueous CH$_3$CN gradient. Final purification of the enriched eluate was achieved by reverse-phase HPLC under the following conditions: YMC-ODS 20×500 mm column, irregular 15 μ particles; mobile phase: water-methanol 1:4; flow rate 12 mL/min; detection: UV at 210 nm. By this procedure, the two pure components, the compounds of formulas II and III, were isolated and purified.

PHYSICO-CHEMICAL PROPERTIES

Compounds of the formula I and IV were obtained as white crystalline solids. Compounds of formula II and III were white amorphous powders after lyophilization. Compounds I, II and III are soluble in chloroform, dichloromethane and dimethyl sulfoxide; partially soluble in ethyl acetate, methanol and acetone; insoluble in water, petroleum ether and hexane. Compound IV is soluble in dichloromethane, chloroform and acetone; partially soluble in ethyl acetate, hexane, methanol and dimethyl sulfoxide; insoluble in water. The compounds were negative in ninhydrin and rydon tests. The physico-chemical properties of these four compounds of this invention are summarized in Table 1.

STRUCTURE ELUCIDATION OF THE COMPOUNDS OF THIS INVENTION

The structures of the compounds of formulas I, II, III and IV were determined based upon spectroscopic data analyses, including MS, UV, IR, $^1$H and $^{13}$C NMR methods. The relative stereochemistry of the compounds I-IV was determined based on the single crystal x-ray crystallographic analysis of the compound of formula I as well as by the correlation study based on the NMR spectral data for the compounds of formulas I to IV. $^1$H and $^{13}$C NMR data are shown in Table 2 and 3. The x-ray crystallographic data is shown in Table 4. Assignments of the protons to the relevant carbons were made by heteronuclear correlated (HETCOR) experiments and the quaternary carbons were located by Distortionless Enhancement of Polarization Transfer (DEPT) as well as Selective Insensitive Nuclei Enhanced Through Polarization Transfer (SINEPT) experiments.

TABLE 1

Physico-chemical Properties of Compounds of formulas I, II, III and IV

| | I | II | III | IV |
|---|---|---|---|---|
| M.P. °C. | 204–205 | 58–60 | 78–80 | 73 |
| Molecular Formula | $C_{20}H_{28}O_3$ | $C_{20}H_{30}O_4$ | $C_{20}H_{30}O_4$ | $C_{20}H_{32}$ |
| Cl-MS (m/z)[1] | 317(M + H)+ | 335(M + H)+ | 335(M + H)+ | 273(M + H)+ |
| El-HRMS (m/e)[2] | Calcd 316.2038 | 334.2144 | 334.2144 | 272.2504 |
| | Found 316.2034 | 334.2147 | 334.2155 | 272.2499 |
| $[\alpha]^{22}(CHCl_3)$ | +224.4° (C. 0.3) | +74.4° (C. 0.24) | +245.6 (C. 0.3) | +110.2° (C. 0.3) |
| UV(MeOH)$\lambda_{max}$nm | End, 244(6,352) | End | End | End |
| IR(KBr)p98 $_{max}$cm$^{-1}$ | 2977, 2887, 1705, 1689, 1625, 1433, 1384, 1198, 896 | 3433, 2918, 2874, 1632, 1448, 1237, 1058, 884 | 3431, 2926, 2856, 1623, 1453, 1232, 1053, 962 | 3013, 2957, 2906, 2843, 1625, 1447, 1383, 901, 861 |

[1]Chemical Ionization Mass Spectra
[2]Election Impact High Resolution Mass Spectra

TABLE 2

$^1$H NMR chemical shift assignments and coupling data of Compounds of Formulas I, II, III and IV

| Proton | I | II | III | IV |
|---|---|---|---|---|
| 1-CH | 3.80 br.s | 41.6–4.24 m | 3.06 OH** | 1.07–1.18 m |
| 3-CH | 6.96 br.s | 3.19 OH** | 4.11 br.s | 5.28 d(J = 3.0 Hz) |
| 4-CH$_2$ | 186–2.68 m | 1.42–1.93 | 1.61–1.72 | 1.90–2.45 m |
| 5-CH | 1.50–1.65 m | 2.10–7.22 m | 2.67–2.82 m | 1.55–1.68 m |
| 7-CH$_2$ | 1.75 dd(J = 7.8, 14.3 Hz) | 1.58–2.41 m | 1.68–2.35 m | 1.45–2.08 m |
| 8-CH$_2$ | 1.88–2.35 m | 1.70–1.98 m | 1.92–2.49 m | 2.07–2.27 m |
| 10-CH | 5.23 br.d(J = 12.1 Hz) | 4.90 br.d(J = 8.7 Hz) | 5.42 br.d(J = 11.7 Hz) | 4.95 br.t(J = 6.5 Hz) |
| 11-CH$_2$ | 1.90–244 m | 1.53–2.42 m | 1.32–2.45 m | 1.90–2.28 m |
| 12-CH$_2$ | 1.12–2.10 m | 1.55–2.00 m | 1.15–1.81 m | 1.20–1.90 m |
| 14-CH | 3.47 s | 2.92 s | 3.62 br.s | 5.11 t(J = 7.2 Hz) |
| 15 | — | 4.16 OH** | 4.19 OH** | 2.60–2.85 m(CH$_2$) |
| 16 | 9.90 d(J = 1.2 Hz, CHO) | 4.30 dd(J = 3.0, 13.2 Hz) 4.50 dd(J = 1.6, 13.2 Hz) | 4.47, 4.72 AB q (J = 12.9 Hz) | 0.84 d(J = 7.1 Hz) |
| 17-CH$_3$ | 0.88 d(J = 7.1 Hz) | 0.91 d(J = 7.1 Hz) | 0.91 d(J = 7.2 Hz) | 1.11 d(J = 7.0 Hz) |
| 18-CH$_3$ | 1.32 s | 1.51 s | 1.23 s | 0.91 s |
| 19-CH$_3$ | 1.60 s | 1.64 s | 1.63 s | 1.55 s |
| 20-CH$_3$ | 1.11 s | 0.99 s | 0.89 s | 1.50 s |

*Measured at 300 MHz in CDCl$_3$; chemical shifts in ppm from TMS.
**Exchangeable with D$_2$O, and assignments are interchangeable.

TABLE 3

$^{13}$C NMR chemical shift assignments of Compounds I, II, III and IV[a]

| Carbon | I | II | III | IV |
|---|---|---|---|---|
| 1 | 53.00 d[b] | 63.83 d | 127.2 s | 40.85 d |
| 2 | 133.3 s | 131.9 s | 144.0 s | 134.2 s |
| 3 | 137.9 d | 148.1 s | 61.03 d | 121.3 d |
| 4 | 30.95 t | 32.47 t | 32.95 t | 30.94 t |
| 5 | 35.95 d | 30.89 d | 26.52 d | 37.12 d |
| 6 | 40.15 s | 38.35 s | 36.90 s | 38.23 s |
| 7 | 34.35 t | 34.19 t | 33.55 t | 39.51 t |
| 8 | 24.69 t | 23.66 t | 24.90 t | 24.22 t |
| 9 | 137.9 s | 134.4 s | 129.1 s | 136.5 s |
| 10 | 125.0 d | 128.5 d | 130.4 d | 122.6 d |
| 11 | 35.02 t | 34.97 t | 36.49 t | 33.04 t |
| 12 | 38.06 t | 38.35 t | 37.32 t | 33.55 t |
| 13 | 63.26 s | 60.49 s | 79.16 s | 139.1 s |
| 14 | 64.18 d | 66.45 d | 73.97 d | 127.3 d |
| 15 | 203.0 s | 108.1 s | 108.4 s | 34.60 t |
| 16 | 193.7 d | 69.48 t | 71.55 t | 17.08 q |
| 17 | 17.43 q | 16.85 q | 16.33 q | 13.25 q |
| 18 | 21.809 q | 21.42 q | 21.59 q | 21.67 q |
| 19 | 16.00 q | 20.94 q | 18.90 q | 16.56 q |
| 20 | 14.41 q | 14.38 q | 14.51 q | 14.98 q |

[a]Recorded at 75 MHz in CDCl$_3$, chemical shifts in ppm from TMS.
[b]Multiplicity was determined by DEPT data.

TABLE 4

X-Ray Crystallographic Data of Compound I[a]

| | |
|---|---|
| Molecular Formula | $C_{20}H_{28}O_3$ |
| Molecular Formula Weight | 316.44 |
| Crystal System | monoclinic |
| Space group | $P2_1 (C_2^2)$ - No. 4 |
| a(Å) | 10.10(1) |
| b(Å) | 11.538(1) |
| c(Å) | 8.237(1) |
| β(°) | 112.93(1) |
| No. of orientation refls.; θ (°) range | 25; 40–45 |
| V(Å$^3$) | 884.1(3) |
| Z | 2 |
| D$_{calcd.}$ (g cm$^{-3}$) | 1.189 |
| μ(Cu—Kα radiation, λ = 1.5418 Å) (cm$^{-1}$) | 5.8 |
| Temp. (°C.) | 23 |
| Crystal dimensions (mm) | 0.05 × 0.20 × 0.40 |
| $T_{max.}$:$T_{min.}$ | 1.00; 0.76 |
| Scan type | ω-2θ |
| Scanwidth (°) | 1.20 + 0.14tanθ |
| θmax. (°) | 75 |
| Intensity control refls.; Variation; repeat time (hr) | 3 1 3; 1 $\bar{1}$ 1; 1 $\bar{3}$ 1, $\bar{1}$ $\bar{3}$ 1; <2%; 2 |
| Total no. of refls. (+h, −k, +l) recorded | 2042 |
| No. of non-equiv. refls. recorded | 1911 |
| $R_{merge}$ (on I) | 0.024 |
| No. of refls. retained [I > 3.0σ(I)] | 1360 |
| No. of parameters refined | 320 |
| Extinction correction | 1.8(1) × 10$^{-6}$ |
| R, R$_w$[b] | 0.045 (0.060) |
| Goodness-of-fit[b] | 1.24 |
| Max. shift:esd in final least-squares cycle | 0.02 |
| Final Δρ (e/Å$^3$)max.; min. | 0.18; −0.15 |

FOOTNOTES FOR TABLE 4

[a]An Enraf-Nonius CAD-4 diffractometer (Cu-Kα radiation, incident-beam graphite monochromator) was used for all measurements. Intensity data were corrected for the usual Lorentz and polarization effects; an empirical absorption correction was also applied.

The crystal structure of the compound of formula I was solved by direct methods (RANTAN). Initial non-hydrogen atom positions were derived from an E-map. Hydrogen atoms were all located in a difference Fourier synthesis evaluated following several rounds of full-matrix least-squares adjustment of non-hydrogen atom positional and thermal (at first isotropic, then an isotropic) parameters, and their positional and isotropic thermal parameters were included as variables in the subsequent least-squares iterations. An extinction correction was also refined during the final rounds of least-squares calculations.

Crystallographic calculations were performed om PDP11/44 and MicroVAX computers by use of the Enraf-Nonius Structure Determination Package (SDP). For structure-factor calculations, neutral atom scattering factors were taken from *International Tables for X-Ray Crystallography*, vol. IV, The Kynoch Press, Birmingham, England, 1974.

[b]$R = \Sigma ||F_o| - |F_c||/\Sigma|F_o|$;
$R_w = [\Sigma w(|F_o| - |F_c|^2)/\Sigma w|F_o|^2]^{\frac{1}{2}}$;
$\Sigma w \Delta^2 [w = 1/\sigma^2(|F_o|), \Delta = (|F_o| - |F_c|)]$ was minimized; Goodness-of-fit = $[\Sigma w \Delta^2/(^N\text{observations} - ^N\text{parameters})]^{\frac{1}{2}}$.

The structures of the four compounds of this invention were determined by spectroscopic data analysis to have the bicyclic diterpene structures represented by formula I, II, III, IV. For example, Compound I has keto, expoxy, olefin and aldehyde functional groups; Compound IV is a triene. As shown hereinbelow, Compounds of formulas I–IV; unlike the diene alcohol verticillol of formula A, do not follow the isoprene rule in that there is no methyl group at the carbon-1 (but there is a methyl group at C-1 ) in verticillol and there is a methyl group at the carbon-6 of IV but there is no methyl group at C-6 of verticillol.

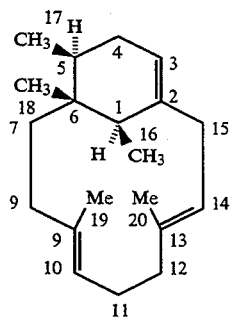

IV

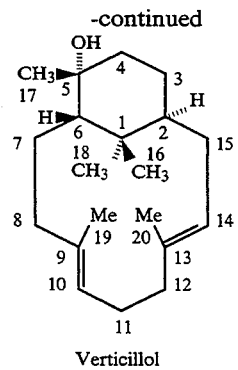

Verticillol

Phomactin B represented by formula B (shown hereinabove) has some but not all of the structural features found in the compounds of this invention. Whereas Phomactin B contains an allylic 1,4 dialcoholic moiety, none of the compounds of this invention possess an allylic dialcohol moiety, and the only mono-alcoholic moiety (a 3-vinyl alcoholic and a 3-allylic alcoholic moiety) is found in the compounds of formula II or III, respectively. The compound of formula IV is a triene and the compounds of formula II and III each contain a hemi-ketal moiety. The compound of formula I possesses an aldehyde moiety but not an alcohol moiety at C-1. Thus, the compounds of this invention are clearly structurally different compared to Phomactin B.

BIOLOGICAL ACTIVITY OF THE COMPOUNDS OF THIS INVENTION

The compounds of formulas I, II, III and IV possess platelet-activating factor ("PAF") antagonistic properties. The compounds are, therefore, useful when PAF is a factor in the disease or disorder. Such disease or disorder includes but is not limited to allergic disease such as asthma, adult respiratory distress syndrome, urticaria and inflammatory diseases such as rheumatoid arthritis and osteoarthritis. For example, PAF is an important mediator of such processes as platelet aggregation, smooth muscle contraction (especially in lung tissue), vascular permeability and neutrophil activation. Recent evidence implicates PAF as an underlying factor involved in airway hyperreactivity, shock, edema, hypersensitivity, disseminated loss of platelets by pregnant women, and in diseases associated with implantation of embryo in utero, in particular.

The PAF antagonistic properties of the compounds of formulas I, II, III and IV may be demonstrated by use of standard pharmacological testing procedures as described below. The in vitro assay procedure is a standard test used to determine PAF antagonistic activity and to evaluate the usefulness of said compounds for counteracting the biological effects of PAF.

A. PAF ANTAGONISM ASSAY

In Vitro Assay

Preparation of Platelet-Rich Plasma (PRP): Human blood (50 ml) is collected from healthy male donors. The blood is mixed with an anticoagulant solution (5 ml) containing sodium citrate (3.8%) and dextrose (2%). Blood is centrifuged at 200×g for 20 min. and the supernatant PRP is carefully transferred into a polypropylene tube. Platelet-poor-plasma (PPP) is prepared by centrifuging PRP at 800×g for 15 min. in a Beckman Microfuge B. PRP is used within 3 hours of drawing the blood.

Platelet Aggregation Assay: When an aggregating agent such as PAF is added to PRP, platelets aggregate. An aggregometer quantifies this aggregation by measuring light (infra-red) transmission through PRP and comparing it to transmission through PPP. The aggregation assays are performed using a dual-channel aggregometer (Model 440, Chrono-Log Corp., Havertown, Pa.). PRP (0.45 ml) in aggregometer curettes is continually stirred (37° C.). Solutions of test compounds in DMSO or vehicle alone (final concentration of DMSO=0.1% v/v) are added to the PRP, and, after incubation for 2 min., 10-15 µl aliquots of PAF solution are added so as to achieve a final concentration of $1-5 \times 10^{-8}M$. Incubations are continued until the increase in light transmission reaches a maximum (usually about 2 min). Values for inhibition are calculated by comparing maximal aggregation obtained in the absence and the presence of the compound. For each experiment, a standard PAF antagonist, such as alprazolam, is used as a positive internal control The inhibitory concentration is the concentration of compound in micromoles at which the indicated % inhibition of the aggregation is found, as measured by the light transmission through each sample of PRP as compared to that through each sample of PPP. Table 5 below presents data for PAF aggregate inhibitory concentrations.

TABLE 5

In vitro PAF activity of the compounds of Formula I-IV in the PAF-Induced Human Platelet Aggregation Assay

| PAF Activity | I | II | III | IV |
|---|---|---|---|---|
| $IC_{50}$ (µM) | 6.96 | 1.68 | 1.26 | >36 |

The compounds of formulas I, II, III, IV can be administered by any therapeutically useful method, such as orally, topically or parenterally, in single or divided daily dose. When used orally or parenterally for the treatment of inflammation, the compounds of formula can be administered in an amount ranging from about 0.01 mg/kg to about 100 mg/kg, preferably from 0.1 mg/kg to about 10 mg/kg per day.

Determination of the proper dosage of a compound of formula I, II, III and IV for a particular situation is within the skill of the art. Generally, treatment is initiated with small dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formulas I, II, III and IV and the pharmaceutically acceptable salts thereof will be regulated according to the judgement of the attending clinician considering such factors as age, condition and size of the patient as well as severity of the symptom being treated. A typical recommended dosage regimen is oral administration of from 10 to 750 mg/day, in two to four divided doses to achieve relief to the symptoms.

Compounds of formulas I, II, III and IV may be administered by any suitable mode, e.g., orally, parenterally, intravenously, topically, etc., as explained further below, depending upon the allergic or inflammatory condition being treated.

For preparing pharmaceutical compositions from the compounds of formulas I, II, III and IV the compounds may be mixed with inert, pharmaceutically acceptable carriers which can be either solid or liquid. Solid form preparations include but are not limited to powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The active ingredient contained in the powders or tablets preferably ranges from about 5 to about 70 percent of the tablet or powder weight. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting was such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

liquid form preparations include solutions, suspensions and emulsions. As an example may be mentioned water or water-propylene glycol solutions for parental injection. Liquid preparations can also be formulated in solution in aqueous polyethylene glycol solution.

Liquid form preparations may also include solutions for intranasal administration.

Aerosol preparations suitable for inhalation may also include solutions and solids in powder form, which may be in combination with a pharmaceutically acceptable carrier, such as an inert compressed gas.

Also included are solid form preparations which are intended to be convened, shortly before use, to liquid form preparations for either oral or parenteral administration. Such liquid forms include solutinos, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweetners, dispersants, thickeners, solubilizing agents and the like.

The compounds of formulas I, II, Ill, and IV may be applied topically, e.g., to the skin, eyes, nose or lungs. Dermatitis, urticaria, acne, and psoriasis exemplify skin conditions in which the compounds are useful. Conjunctivitis, rhinitis, and asthma are examples of diseases or conditions in which the compounds may be advantageously applied to eyes, nose and lungs, respectively.

Formulations for topical application, e.g., for use in treating psoriasis, may include the above liquid forms, creams, aerosols, sprays, dusts, powders, lotions, drops and ointments which are prepared by combining an active ingredient according to this invention with conventional pharmaceutical diluents and carriers commonly used in topical dry, liquid, cream and aerosol formulations.

The topical pharmaceutical compositions according to the invention may also contain other active ingredients such as antimicrobial agents, particularly antibiotics, anesthetics, analgesics and antipruritic agents.

The compounds of formulas I, II, III and IV may also be deliverable transdermally. The transdermal compositions can take the form of creams, lotions, aerosols and/or emulsions and can be included in a transdermal patch of the matrix or reservoir type as is conventional in the art for this purpose.

The pharmaceutical preparation is preferably in unit dosage form. In such form, the preparation is subdivided into unit doses containing appropriate quantities of the active component, e.g., from 0.1 to 1000 mg, preferably from 1 mg to 100 mg, accordingly to the particular application. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these is packaged form.

The following example is intended to illustrate, but not to limit, the present invention.

EXAMPLE 1

The initial stage inoculum for the fermentation of the PAF antagonist compounds was prepared by transferring 2.5 ml of a frozen whole broth to 50 ml of germination medium in 250 ml Erlenmeyer flasks. The germination medium consisted in grams/liter of proteose peptone #3, 5.0; sodium chloride, 5.0; cerelose, 20.0; yeast extract, 3.0; soy grits, 5.0; and sodium potassium phosphate (monobasic) 5.0. The pH of the medium was adjusted to 7.0 prior to sterilization. The flasks were incubated at 30° C. on a gyratory shaker at 300 rpm for 48 hours. For the second stage germination, a 2 liter Erlenmeyer flask containing 350 ml of the same medium was inoculated with 25 ml of the first stage germination. These were incubated as described above but for 72 hours. Ten liter fermentations were carried out in 14 liter fermenters (New Brunswick Scientific, Edison, N.J.) in a medium containing, in grams/liter, neopeptone, 10.0; and ceretose, 40.0 The pH of the medium was adjusted to 7.0 before sterilization. The second stage inoculum (3.5%) was used to initiate the fermentation which was conducted at 30° C. with 4.5 L/min. air flow and 400 rpm agitation for five days. An anti foam agent such as SAG (Union Carbide Corp., 50% solution) is added, if necessary to the fermenters to control foam. During the course of the fermentation, PAF-active complex was monitored by the PAF-induced platelet aggregation assay of the whole broth. The isolation and purification of the PAF-active complex and of the compounds of formula I to IV is described herein above.

What is claimed is:

1. A compound represented by the formulas I, II, III or IV:

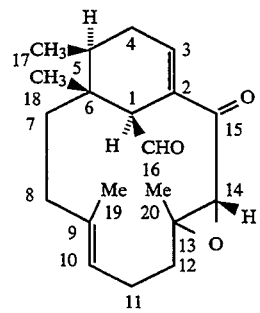

I

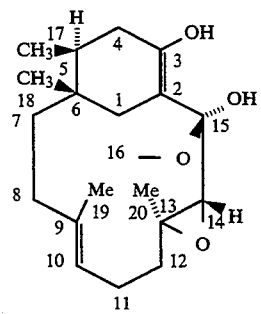

II

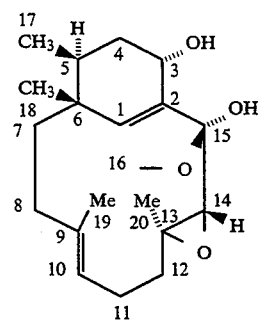

III or

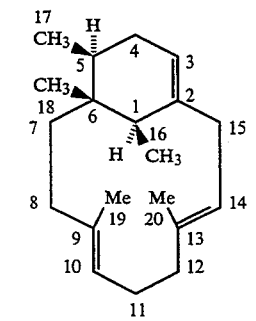

IV in chemically pure form.

2. A pharmaceutical composition comprising a compound represented by a formula I, II, III or IV of claim 1 and a pharmaceutically acceptable carrier therefor.

* * * * *